United States Patent
Smirnov et al.

(10) Patent No.: US 6,741,362 B2
(45) Date of Patent: May 25, 2004

(54) METHOD, SYSTEM, AND COMPUTER PROGRAM PRODUCT FOR DETERMINING REFRACTIVE INDEX DISTRIBUTION

(75) Inventors: Stanislav Smirnov, Bethel, CT (US); Mark L. Oskotsky, Mamaroneck, NY (US); Lev Sakin, Stamford, CT (US); John D. Martin, Wallingford, CT (US)

(73) Assignee: ASML Holding N.V., Veldhoven (NL)

( * ) Notice: Subject to any disclaimer, the term of this patent is extended or adjusted under 35 U.S.C. 154(b) by 8 days.

(21) Appl. No.: 10/138,714

(22) Filed: May 6, 2002

(65) Prior Publication Data

US 2002/0191193 A1 Dec. 19, 2002

Related U.S. Application Data

(60) Provisional application No. 60/288,782, filed on May 7, 2001.

(51) Int. Cl.[7] ............... G01N 21/41; G01J 4/00; G01J 5/52; G01B 9/02; G01B 11/02
(52) U.S. Cl. ............ 356/517; 356/365; 356/477; 356/48; 356/484; 356/504; 356/513; 356/517
(58) Field of Search ............... 356/365, 481, 356/484, 485, 477, 488, 517, 494, 504, 513, 515

(56) References Cited

U.S. PATENT DOCUMENTS

| | | | |
|---|---|---|---|
| 5,303,033 A | | 4/1994 | Matsuzaki ............ 356/345 |
| 5,526,118 A | * | 6/1996 | Miyagawa et al. |
| 5,557,408 A | | 9/1996 | Kanaya ............ 356/359 |
| 6,157,448 A | * | 12/2000 | Kowa et al. |

OTHER PUBLICATIONS

S. G. Lipson et al., "Optical Physics," Third Edition, Chapter Nine, Interferometry, Cambridge University Press, 1995, pp. 232–252.

Grant R. Fowles, "Introduction to Modern Optics," Second Edition, Chapter 3, Coherence and Interference, Dover Publications, Inc., New York, 1989, pp. 62, 69.

* cited by examiner

*Primary Examiner*—Frank G. Font
*Assistant Examiner*—Khaled Brown
(74) *Attorney, Agent, or Firm*—Sterne, Kessler, Goldstein & Fox, P.L.L.C.

(57) ABSTRACT

The present invention provides a method and system for determining three-dimensional refractive gradient index distribution. The method and system of the present invention determine inhomogeneity data and calculate index of refraction changes in three-dimensions (3D). The method and system provide 3D modeling of an optical object or system that determines the three-dimensional distribution of the refractive index in the object. In one embodiment, the optical object is a blank. In different embodiments, the optical system is more than one blank. In alternative embodiments, the optical system can be a projection optics system that can include optical components such as lenses, filters, plates, and prisms. The present invention also provides a method for selecting a plurality of preferred optical elements to assemble a composite optical system with predetermined parameters.

25 Claims, 13 Drawing Sheets

METHOD, SYSTEM, AND COMPUTER PROGRAM PRODUCT FOR DETERMINING REFRACTIVE INDEX DISTRIBUTION

CROSS-REFERENCE TO RELATED APPLICATIONS

This application claims the benefit of U.S. Provisional Application No. 60/288,782, filed May 7, 2001, which is incorporated herein by reference.

BACKGROUND OF THE INVENTION

1. Field of the Invention

The present invention relates generally to optics and, in particular, to determining refractive index distribution in optics for microlitography.

2. Description of the Related Art

Improvement in the manufacturing accuracy of optical components requires more accurate techniques for measuring the properties of optical components.

A two-dimensional (2D) radial model of gradient index (GRIN) is a measuring technique that can be used to estimate the inhomogeneity of optical materials, such as glass or crystals. The existing 2D GRIN techniques estimate the inhomogeneity in two directions, defined according to a Cartesian axis system.

A 2D radial model for GRIN measurement is used to obtain approximate refractive index description. The 2D radial model estimates the inhomogeneity of the optical material by assuming that the refractive index can vary only in two directions. It also assumes that inhomogeneity is constant through the optical material, along a third Cartesian direction. These assumptions greatly simplify the method, system, and computational complexity required to determine the refractive index, encompassed in a workable range. But they introduce a relatively wide range of error.

As the requirements regarding optical components become stricter, the need for more precise measurement methods and systems becomes apparent. What is needed is a technique to determine the three-dimensional refractive gradient index for the optical components.

SUMMARY OF THE INVENTION

The present invention is directed to a method, system and computer program product for determining a three-dimensional refractive gradient index of an object. The object comprises an optical material. The optical material, such as a blank in lithography processes, can be a piece of glass, quartz, plastic or other transparent material, fabricated roughly by molding or shaped into the desired finished part. The method is carried out with an interferometric refractive index measurement system.

First the object is located, with a normal orientation, in the interferometric refractive index measurement system, along a first axis, between a reference surface and a retro-mirror surface. A second and a third axis are normal to each other and normal to the first axis.

Second, first through forth phase differences are measured between: a reference wavefront and a wavefront reflected from a first surface of the object; a reference wavefront and a wavefront reflected from a second surface of the object through the object itself; reference wavefront and wavefront reflected from the surface of the retro-mirror through the object and a reference wavefront and a wavefront reflected from the surface of the retro-mirror without object.

Based on these measurements, first through forth two-dimensional surface deformations are determined for the reference surface, the first surface and the second surface of the object, respectively. An average two-dimensional inhomogeneity of the object is then determined. In one embodiment of the invention, using Zernike polynomials, a plurality of coefficients of approximation are determined.

Further on, the object is moved through a plurality of rotation and positions by angles about the second and the third axis. Phase differences are measured between the reference wavefront and a wavefront reflected from the surface of the retro-mirror through the object for each one of the rotations. A plurality of three-dimensional coefficients of approximation are then determined based on the already-assessed surface deformations. The procedure concludes with the determination of a plurality of $A_{ij}$ coefficients describing a three-dimensional refractive gradient index distribution in the object.

The above method is applied, but not limited to, determining three-dimensional refractive gradient index of lens blank objects, lens objects, of cylindrical volumes of optical material. In the preferred embodiments of the invention, the optical material is glass or plastic.

The interferometric refractive index measurement system is implemented using one of Fizeau, Michaelson, Twyman-Green, Mach-Zehnder or other known or future known interferometers.

In a preferred embodiment of the present invention the source for generating the reference wave front is a laser source.

The invention further provides a method for selecting a plurality of preferred optical elements used to assemble a composite optical system with predetermined parameters. The method comprises the steps of selecting a first through N groups of optical elements, wherein N has a predetermined value, testing each optical element of first through N groups of optical elements, using the above method for determining a three-dimensional refractive gradient index, determining a plurality of optical characteristics for each tested optical element, and selecting at least one preferred optical element from each of first through N groups of tested optical elements, based on the determined optical characteristics to design or otherwise assemble a composite optical system.

Further features and advantages of the invention, as well as the structure and operation of various embodiments of the invention, are described in detail below with reference to the accompanying drawings. It is noted that the invention is not limited to the specific embodiment described herein. Such embodiments are presented herein for illustrative purposes only. Additional embodiments will be apparent to persons skilled in the relevant art(s) based on the teachings contained herein.

BRIEF DESCRIPTION OF THE FIGURES

These and other advantages and features of the present invention will become better understood upon consideration of the following detailed description of the invention when considered in connection with the accompanying drawings, in which like reference numerals designate like parts throughout the figures thereof, and wherein.

DETAILED DESCRIPTION OF THE PREFERRED EMBODIMENTS

Figure 1:
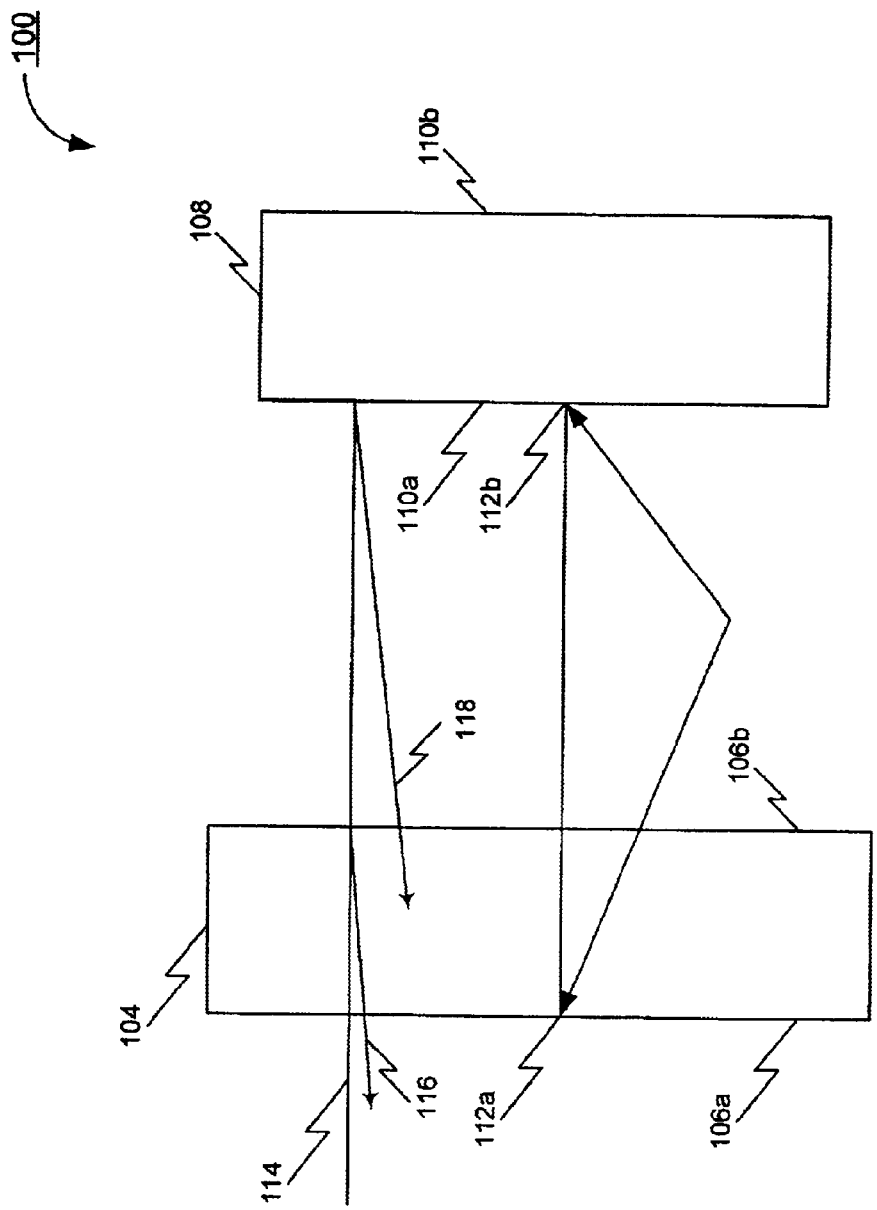
FIG. 1 shows an example implementation of a 2D interferometric refractive index measurement system, indicating the reflections from a reference surface and a first surface of an object comprising an optical material.

The present description is described in terms of the following example environments. It is not intended that the invention be limited to application in these example environments. After reading the following description it will become apparent to a person skilled in the relevant art how to implement the invention in alternative environments.

Gradient Index (GRIN) Measurements

The present invention makes use of interferometric techniques and systems. In one embodiment a Fizeau interferometer is employed.

One or more fiducial marks or spots are placed in the field of view of the interferometric refractive index measurement system to provide a means of reference. Surfaces with such means of reference are called reference surfaces. The same fiducial marks in the interferometric refractive index measurement system can be used to measure different parts of the object.

As one skilled in the relevant art would recognize, the configuration of any interferometer depends on the application to which it is engaged. In terms of the present invention, the embodiments described herein employ the Fizeau interferometer. This is not intended to limit the application of the present invention to the Fizeau interferometers. One skilled in the relevant art, after reviewing the embodiments disclosed herein, would be able to configure a different type of interferometer to perform the present invention. In alternative embodiments of the present invention, a Michelson interferometer, a Twyman-Green interferometer, a Mach-Zehnder or any known or future known interferometer can substitute for the Fizeau interferometer.

A two-dimensional (2D) radial model of gradient index describes the index of refraction (n) as:

$$n(x, y) = n_o + \sum_{i=1}^{s} A_i P_i\left(\frac{x}{M_{xy}}, \frac{y}{M_{xy}}\right), \quad \text{(EQ. 1)}$$

where x, y are the coordinates of a point determined in an x,y,z Cartesian coordinate system; $P_i$ is the i-th Zernike polynomial orthogonal over the circle of unit radius (the center of this circle coincides with the origin of the Cartesian coordinate system); $M_{xy}$ is a normalization radius for the Zernike polynomials; $n_0$ is a bulk refractive index of the object; $A_i$ are coefficients of approximation; and s is the number of Zernike polynomials.

The 2D evaluation of the gradient index of refraction can be done applying two types of radial models: (1) an estimation of the inhomogeneity of the plane parallel object comprising an optical material, using a Fizeau interferometer (an example implementation of an interferometric measurement system is described below in connection with FIGS. 1–4); and (2) an estimation of lens inhomogeneity in a null test scheme (as described below in connection with FIG. 5).

It is noted that the systems and the methods described with regard to FIGS. 1–5 do not obtain three-dimensional (3D) inhomogeneity data. Thus, they do not allow the necessary precise modeling of an object comprising optical material.

First Radial Model

According to the first radial model, the determination of the Ai coefficients is based on four interferometric measurements. The measurements are carried out for normal incidence of a reference wavefront onto the object. For the example embodiments illustrated by the present invention, the measurements are showed in FIGS. 1–4.

FIG. 1 illustrates an example 2D intereferometric refraction index system. Specifically, interferometric system 100 includes a reference element 104 with reference surfaces 106a and 106b. The system 100 also includes an object 108, which comprises an optical material, with first surface 110a and second surface 110b. A laser source (not illustrated in the figure) generates a reference wavefront 114. On the reference surface 106a and on the first surface of the object 110a fiducial marks are placed at points 112a and 112b, as illustrated in FIG. 1. In alternative embodiments, the fiducial marks can be located on the surfaces using passive imaging devices (e.g., cameras) included in the interferometric system 100.

It is noted that in order to simplify FIGS. 1–5, some angles of reflection and refraction are not illustrated. The elimination of these items is not intended to limit the scope of the invention. Persons skilled in the relevant art, based on the teachings described herein, would be able to determine these angles from the illustrations on FIGS. 1–5.

Reference wavefront 114 is incident to the interferometric system 100 and reflects from the various surfaces. The wavefront 114 is designed so that it is generated from an ideal point source, with a surface of constant phase. The reference wavefront 114 reflects from the reference surfaces 106b and the first surface 110a. The reflected beams 116 and 118 are isolated and the phase difference of their wavefronts is measured. The determined phase difference is stored for later surface determination, as described herein.

Figure 2:
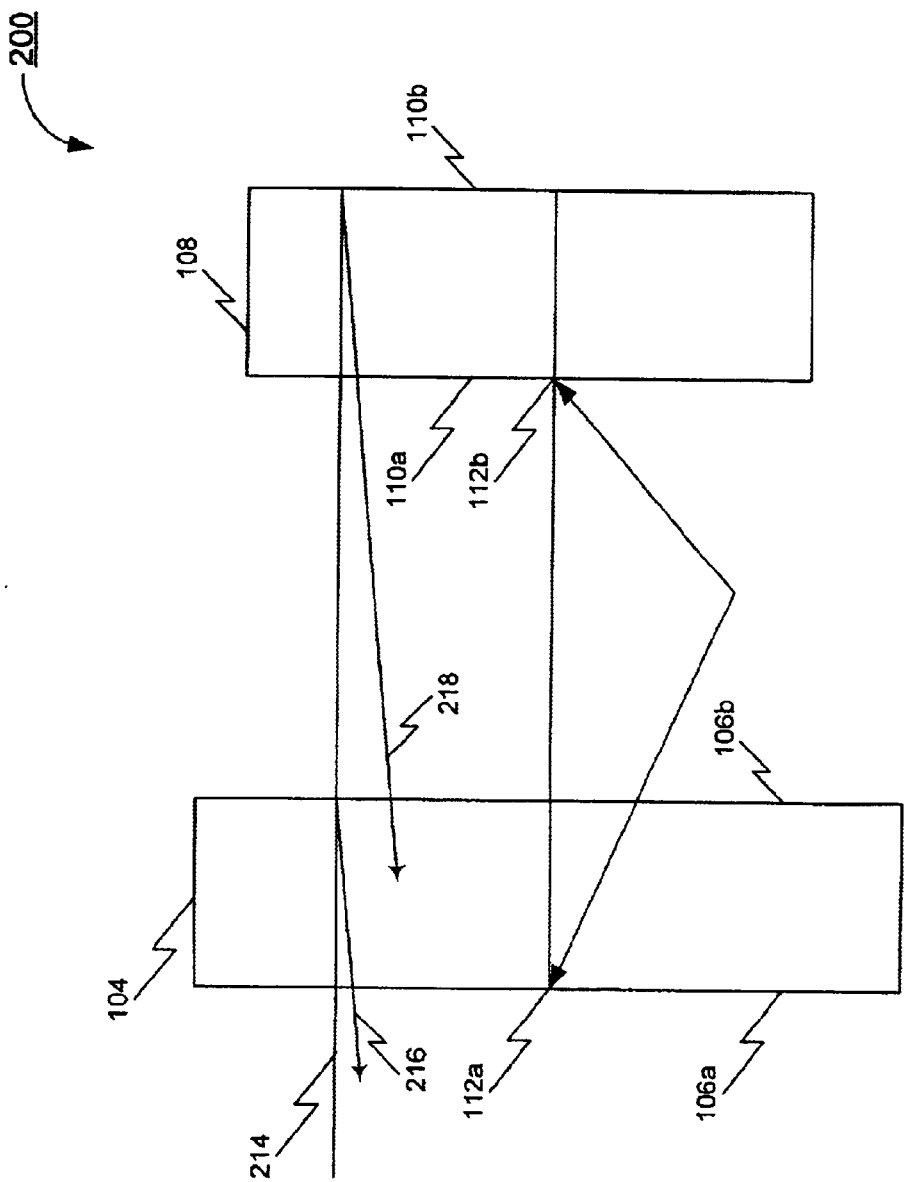
FIG. 2 shows an example implementation of a 2D interferometric refractive index measurement system, indicating the reflections from a reference surface and a second surface of an object comprising an optical material.

FIG. 2 illustrates an exemplary implementation of an 2D intereferometric refraction index system indicating the reflections from a reference surface and a second surface of an object comprising an optical material. Specifically FIG. 2 shows an interferometric arrangement 200 that includes a reference element 104 with reference surfaces 106a and 106b. The system 200 also includes an object, comprising an optical material 108 with first surface 110a and second surface 110b. A laser source (not illustrated in the figure) generates a reference wavefront 214. On the reference surface 106a, and on the first surface of the object 110a, fiducial marks are placed at points 112a and 112b, as illustrated in FIG. 2. In alternative embodiments, the fiducial marks can be placed onto the surfaces using passive imaging devices (e.g., cameras) included in the interferometric system 200.

Reference wavefront 214 is incident to the interferometric system 200 and reflects from the various surfaces. The wavefront 214 is designed so that it is generated from an ideal point source, with a surface of constant phase. The reference wavefront 214 reflects from the reference surfaces 106b and the second surface 110b. The reflected beams 216 and 218, are located, and the phase difference of their wavefronts is measured. The determined phase difference is stored for later surface determination, as described herein.

Figure 3:
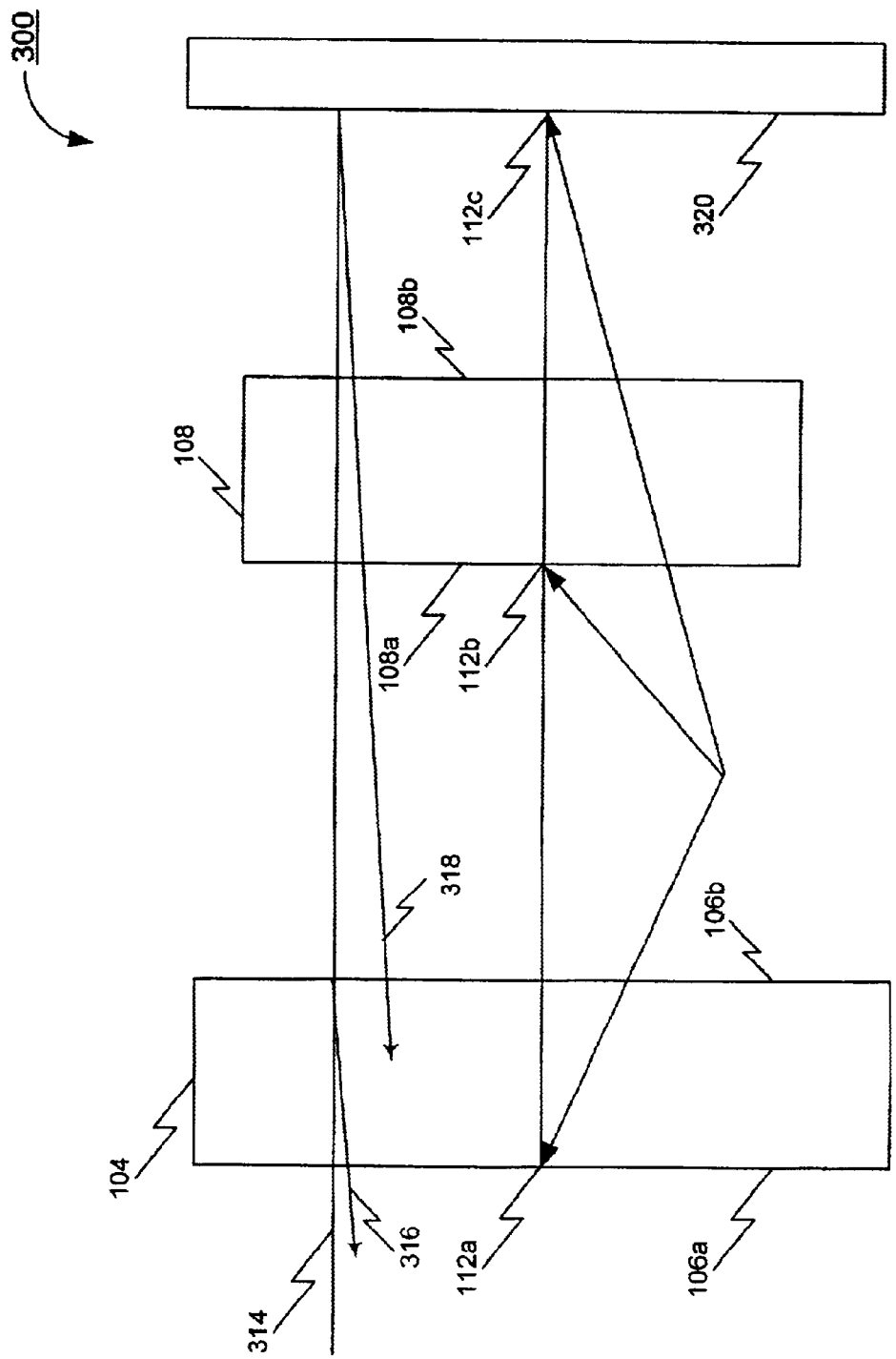
FIG. 3 shows an example implementation of an 2D interferometric refractive index measurement system, indicating the reflections from a reference surface and a surface of a retro mirror, through the object comprising an optical material.

FIG. 3 illustrates an exemplary transmission test for a 2D-intereferometric-refraction index system indicating the reflections from a reference surface and a retro-mirror surface through the object comprising an optical material. FIG. 3 shows an interferometric arrangement 300 that includes a reference element 104 with reference surfaces 106a and 106b and an object comprising an optical material 108 with first surface 108a and second surface 108b. The system 300 also includes a retro-mirror surface 320. A laser source (not illustrated in the figure) generates a reference wavefront 314.

On the reference surface 106a, on the first surface of the object 108a and on the retro-mirror surface 320 fiducial marks are placed at points 112a and 112b and 112c, as illustrated in FIG. 3. In alternative embodiments, the fiducial marks can be placed onto the surfaces using passive imaging devices (e.g., cameras) included in the interferometric arrangement 300.

Reference wavefront 314 is incident to the interferometric system 300 and reflects from various surfaces. The wavefront 314 is designed so that it is generated from an almost point source, with a surface of constant phase. The reference wavefront 314 reflects from the reference surfaces 106b and the retro-mirror surface 320. The reflected beams 316 and 318, respectively, are located and the phase difference of their wavefronts is measured. The determined phase difference is stored for later surface determination, as described herein. Example implementations of the present interefero-metric arrangement may use certified retro-mirrors, with known surface deformation map.

Figure 4:
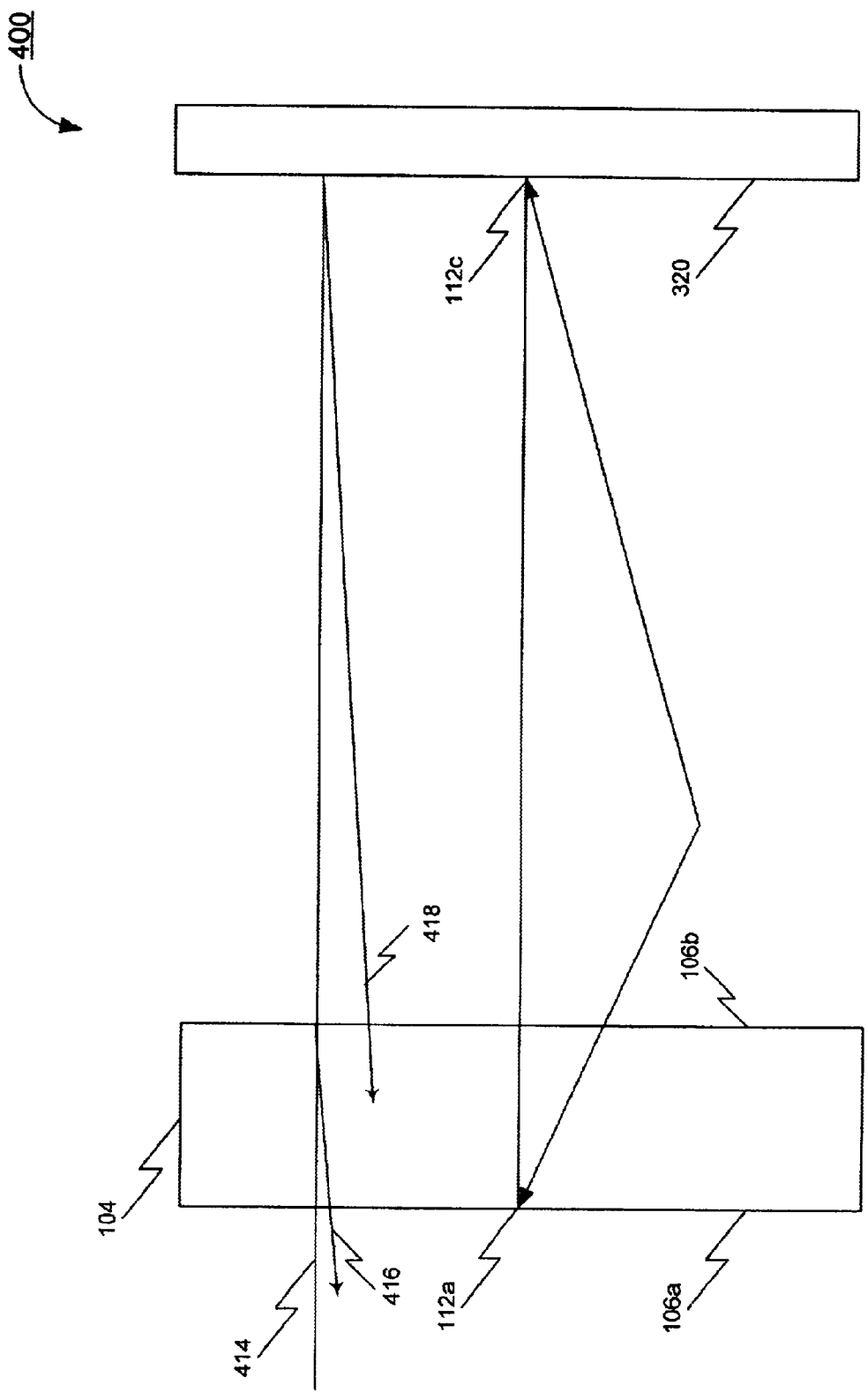
FIG. 4 shows an example implementation of an 2D interferometric refractive index measurement system, indicating the reflection from a reference surface and the surface of a retro mirror without the object comprising an optical material.

FIG. 4 illustrates an exemplary cavity test for a 2D intereferometric refraction index system, indicating the reflections from a reference surface and a retro-mirror surface. FIG. 4 shows an interferometric arrangement 400 that includes a reference element 104 with reference surfaces 106a and 106b and a retro-mirror surface 320. A laser source (not illustrated in the figure) generates a reference wavefront 414.

On the reference surface 106a and on the retro-mirror surface 320 fiducial marks are placed at points 112a and 112c, as illustrated in FIG. 4. In alternative embodiments, the fiducial marks can be placed onto the surfaces using passive imaging devices (e.g., cameras) included in the interferometric arrangement 400.

Reference wavefront 414 is incident to the interferometric system 400 and reflects from various surfaces. The wavefront 414 is designed so that it is generated from an almost point source, with a surface of constant phase. The reference wavefront 414 reflects from the reference surfaces 106b and the retro-mirror surface 320. The reflected beams 416 and 418, respectively, are located and the phase difference of their wavefronts is measured. The determined phase difference is stored for later surface determination, as described herein. Example implementations of the present interefero-metric arrangement may use certified retro-mirrors, with known surface deformation map.

The variation of object's refractive index (inhomogeneity) $\Delta n$ can be calculated using the following formula:

$$\Delta n(x, y) = \frac{1}{d}\{n_0[M_4(x, y) - M_3(x, y)] + (n_0 - 1)[M_2(x, y) - M_1(x, y)]\}, \quad \text{(EQ. 2)}$$

where d is the object's thickness; $M_1(x,y)$, $M_2(x,y)$, $M_3(x,y)$, $M_4(x,y)$ are the measured phase differences corresponding to the same x and y coordinates for the interferometric test illustrated in FIG. 1, the interferometric test illustrated in FIG. 2, the transmission test illustrated in FIG. 3, and the Cavity test shown in FIG. 4, respectively.

An analytical description of the inhomogeneity across the tested object, for an arbitrary point with coordinated x and y is wanted to be obtained. The analytical expression is implemented using two-dimensional polynomials, which are orthogonal over the working area of the object. This working area can be a circle, for example as it is the case of a circular optical object. Examples of polynomials orthogonal over a circular area are Zernike polynomials. As would be apparent to one skilled in the art, the use of Zernike polynomials is only an example. Any other type of polynomials orthogonal over a workable area of the object, of arbitrary shape, can be used.

The inhomogeneity can be approximated using a truncated Zernike series:

$$\Delta n(x, y) = \sum_{i=1}^{S} A_i P_i\left(\frac{x}{M_{xy}}, \frac{y}{M_{xy}}\right), \quad \text{(EQ. 3)}$$

where the terms of the series have the same significance as previously indicated. The $A_i$ coefficients are computed using least square method.

Second Radial Model

According to the second radial model, the 2D approach determines the coefficients $A_i$ based on three interferometric measurements performed with a tested optical object and known parameters of a null test scheme. In one embodiment of the present invention, two interferometric measurements are obtained for the element's surface interferometric data and a third measurement is obtained for transmission data for the element in a null test scheme.

Figure 5:
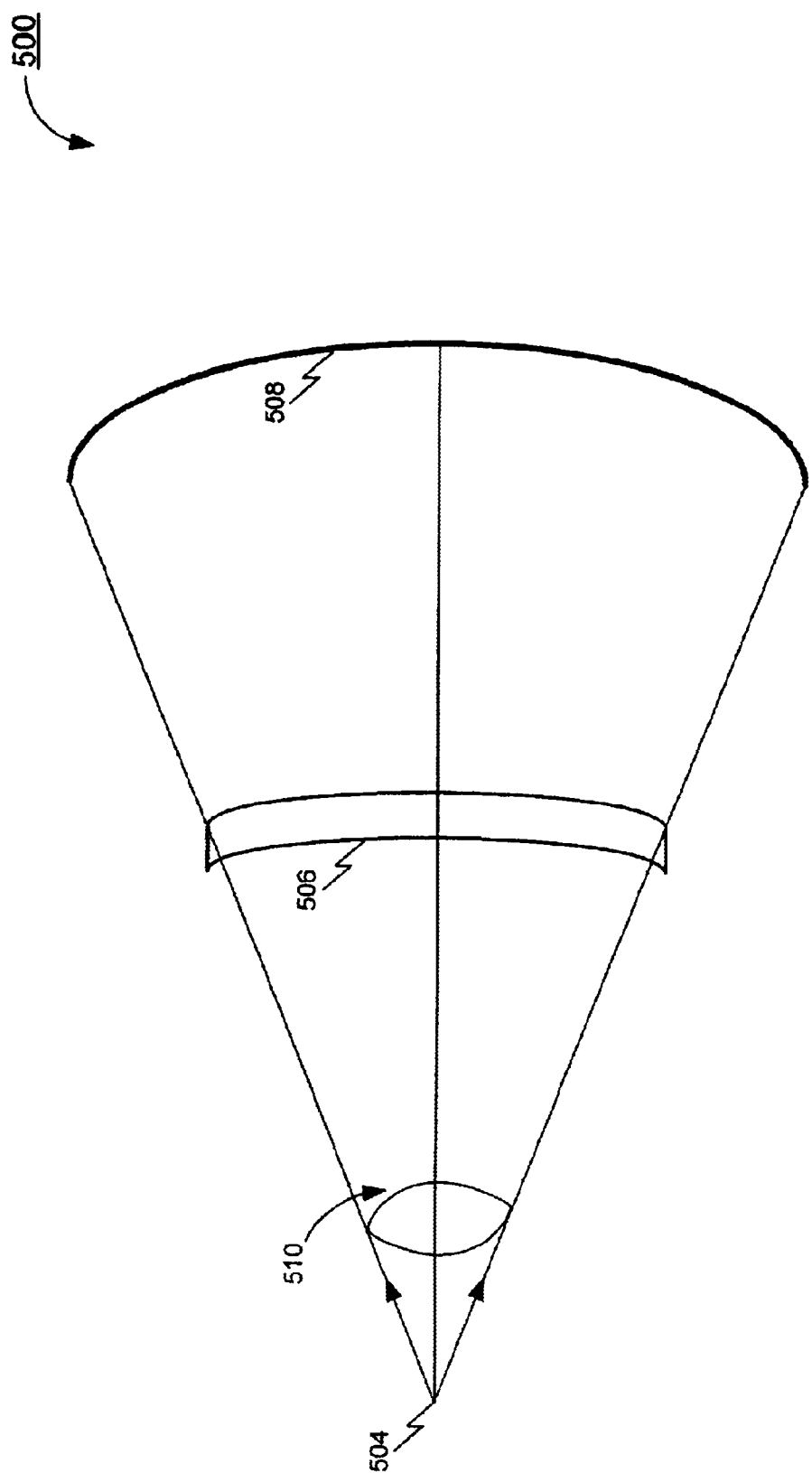
FIG. 5 illustrates a null test scheme for performing measurements of the refractive index distribution for an object comprising an optical material.

FIG. 5 illustrates a null test scheme for determining transmission interferometric measurements of an optical system. In this embodiment, the coefficients $A_i$ are determined using optimization methods to minimize the difference between the measured and modeled transmission null test data obtained An interferometric system 500 includes a light source 504, a lens under test 506, and a mirror 508. It may also include null-corrector element 510.

It is noted that the systems and the methods described with regard to FIGS. 1–5 do not obtain three-dimensional (3D) inhomogeneity data. Thus, they do not allow the necessary precise modeling of an object comprising optical material.

FIGS. 6 through 10 illustrate a three-dimensional interferometric refractive index measurement system used to collect the inhomogeneity data, according to the present invention. The interferometric system comprises a reference surface 104, an object comprising an optical material 108 and a retro-mirror surface 320. The reference system is an x,y,z, Cartesian coordinate system.

Figure 6:
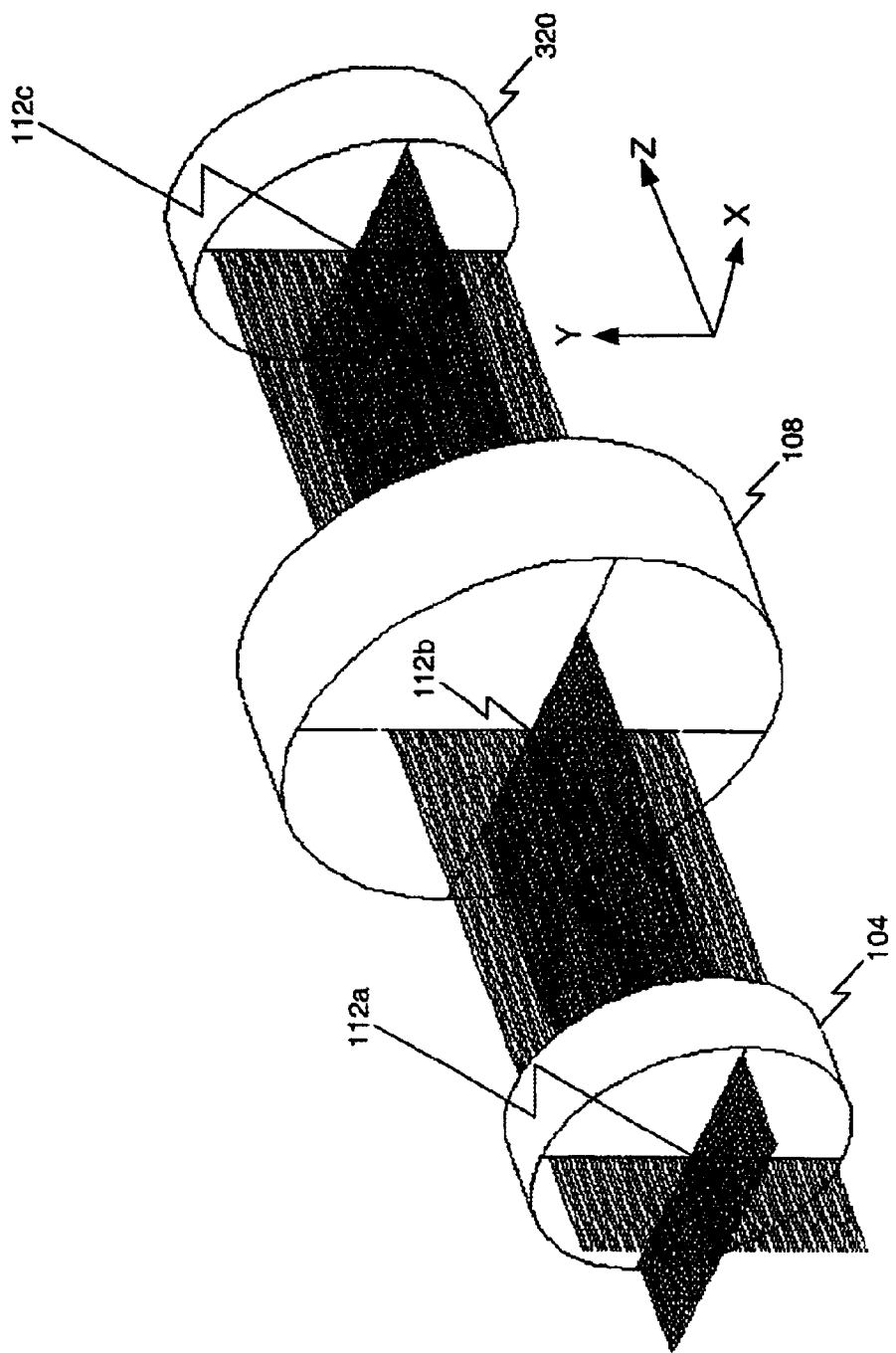
FIG. 6 shows an example of a three-dimensional implementation of an interferometric refractive index measurement system with an object comprising an optical material, that is normally oriented upon the first axis, according to the present invention.

FIG. 6 illustrates a three-dimensional interferometric refractive index measurement system with an object 108 that has normal orientation relative to the reference surface 104 and the retro-mirror surface 320. A laser source (not shown in the figure) generates a wavefront that is reflected by the plurality of surfaces comprised by the interferometric arrangement. A phase difference measurement is performed for the wavefront reflected from the reference surface 104 and the wavefront reflected from the retro-mirror 320 through the object 108. The collected interferometric data (denoted with $M_6$) is stored for later surface deformation determination.

Figure 7:
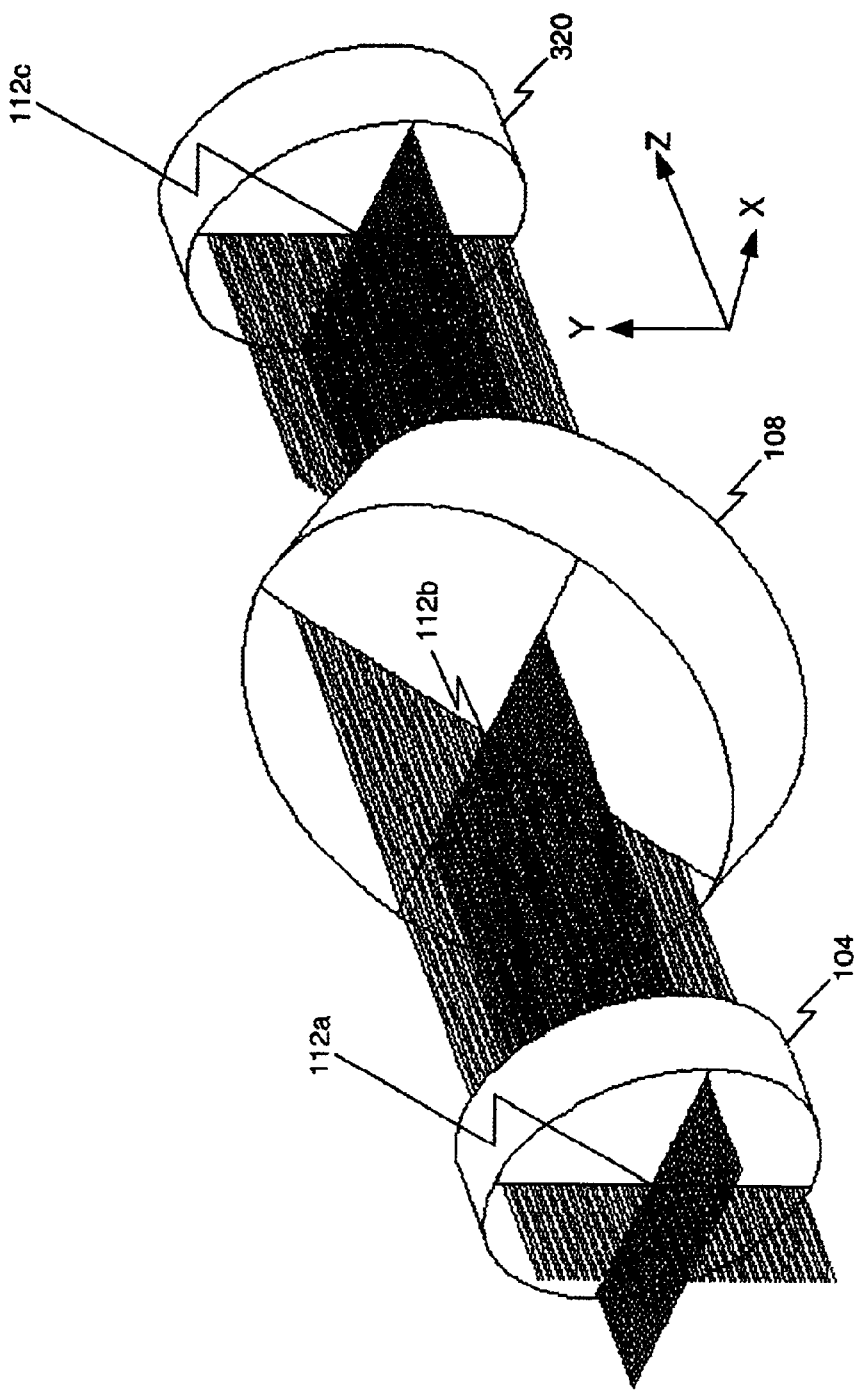
FIG. 7 shows an example of a three-dimensional implementation of an interferometric refractive index measurement system with an object comprising an optical material in a first tilted position upon the second axis, according to the present invention.

FIG. 7 illustrates a three-dimensional interferometric refractive index measurement system with the object 108 having a first tilted position about the second axis. In a preferred embodiment of the present invention, the object 108 is tilted approximately 45 degrees about x axis, towards the retro-mirror surface. A laser source (not shown in the figure) generates a reference wavefront that is reflected by the plurality of surfaces of this interferometric arrangement. A phase difference measurement is determined for the wavefront reflected from the reference surface 104 and the wavefront reflected from the retro-mirror 320 through the titled object 108. The collected interferometric data (denoted with $M_7$) is stored for later surface deformation determination. The position of the retro-mirror surface 320 is adjusted along y axis so that the fiducial marks 112a, 112b, 112c are aligned along one ray.

Figure 8:
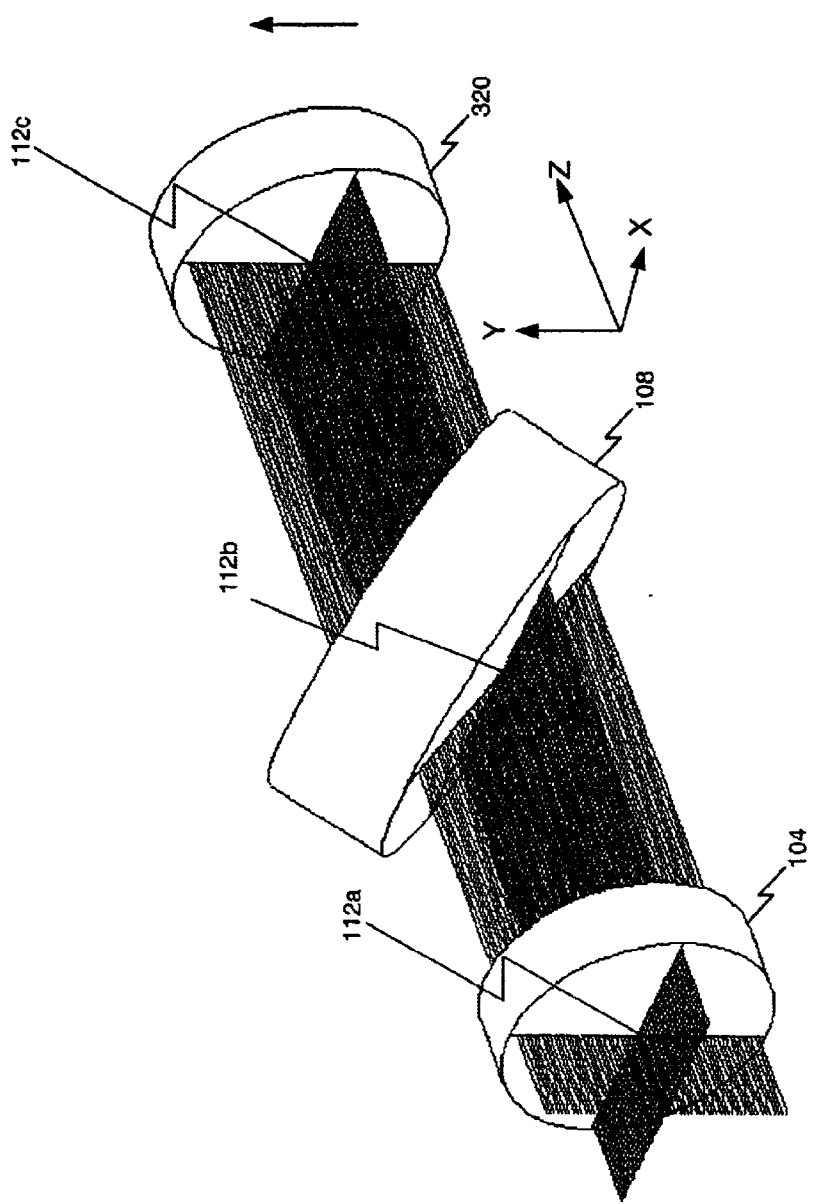
FIG. 8 shows an example of a three-dimensional implementation of an interferometric refractive index measurement system with an object comprising an optical material in a second tilted position upon the second axis, according to the present invention.

FIG. 8 illustrates a three-dimensional interferometric refractive index measurement system with the object 108 having a second tilted position along the second axis. In a preferred embodiment of the present invention the object 108 is tilted approximately 45 degrees about x axis towards the reference surface. A laser source (not shown in the figure) generates a reference wavefront that is reflected by the plurality of surfaces comprised by this interferometric arrangement. A phase difference measurement is determined for the wavefront reflected from the reference surface 104, and the wavefront reflected from the retro-mirror through the titled object 108. The collected interferometric data (denoted with $M_8$) is stored for later surface deformation determination. The position of the retro-mirror surface 320 is adjusted along y axis so that fiducial marks 112a, 112b, 112c are aligned along one ray.

Figure 9:
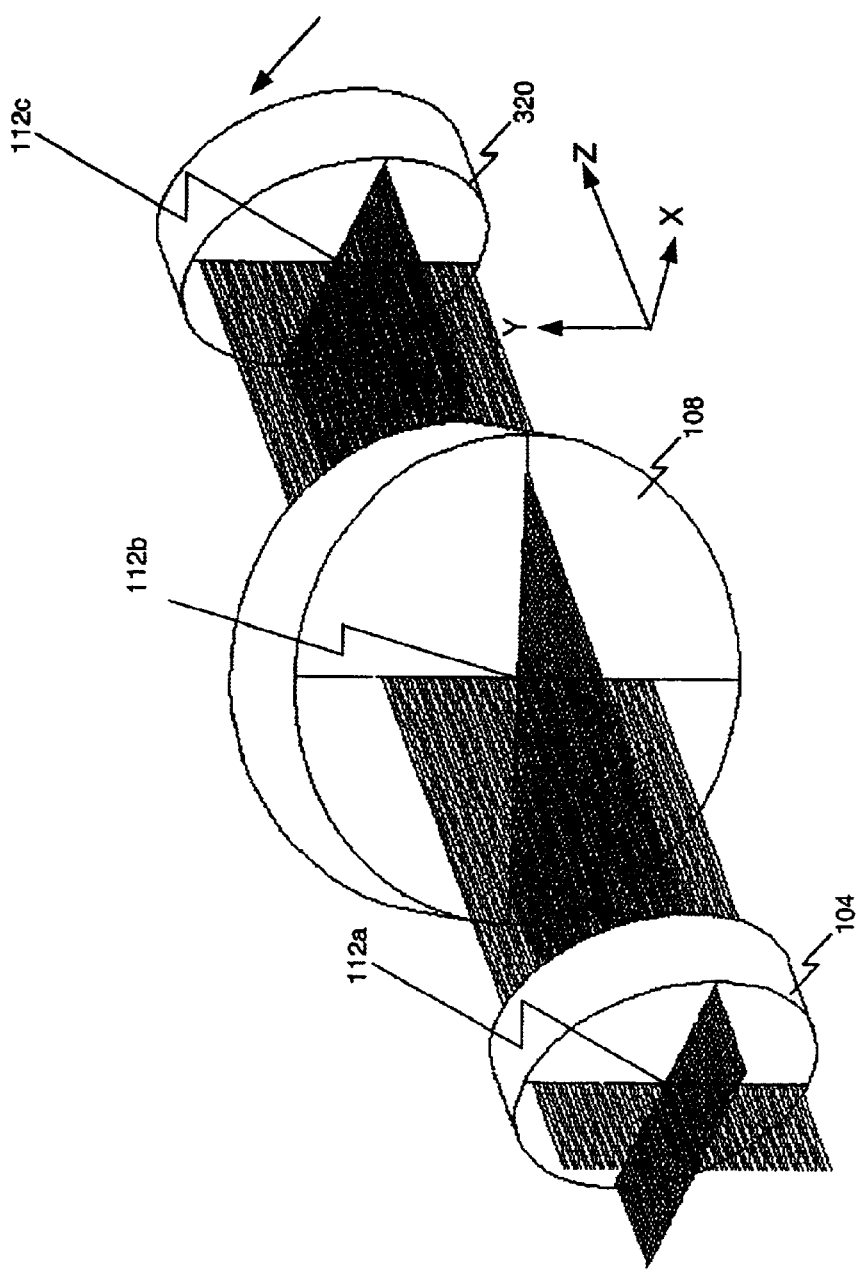
FIG. 9 shows an example of a three-dimensional implementation of an interferometric refractive index measurement system with an object comprising an optical material in a first tilted position upon the third axis, according to the present invention.

FIG. 9 illustrates a three-dimensional interferometric refractive index measurement system with the object 108 having a first tilted position about the third axis. The third axis is normal to the first and second axis, and corresponds to a z y Cartesian axis. In a preferred embodiment of the present invention, the object 108 is tilted approximately 45 degrees y axis, towards the retro-mirror surface. A laser source (not shown in the figure) generates a reference wavefront that is reflected by the plurality of surfaces comprised by this interferometric arrangement. A phase difference measurement is determined for the wavefront reflected from the reference surface 104 and the wavefront reflected from the retro-mirror through the titled object 108. The collected interferometric data (denoted with $M_9$) is stored for later surface deformation determination. The position of the retro-mirror surface 320 is adjusted along x axis so that the fiducial marks 112a, 112b, 112c are aligned along one way.

Figure 10:
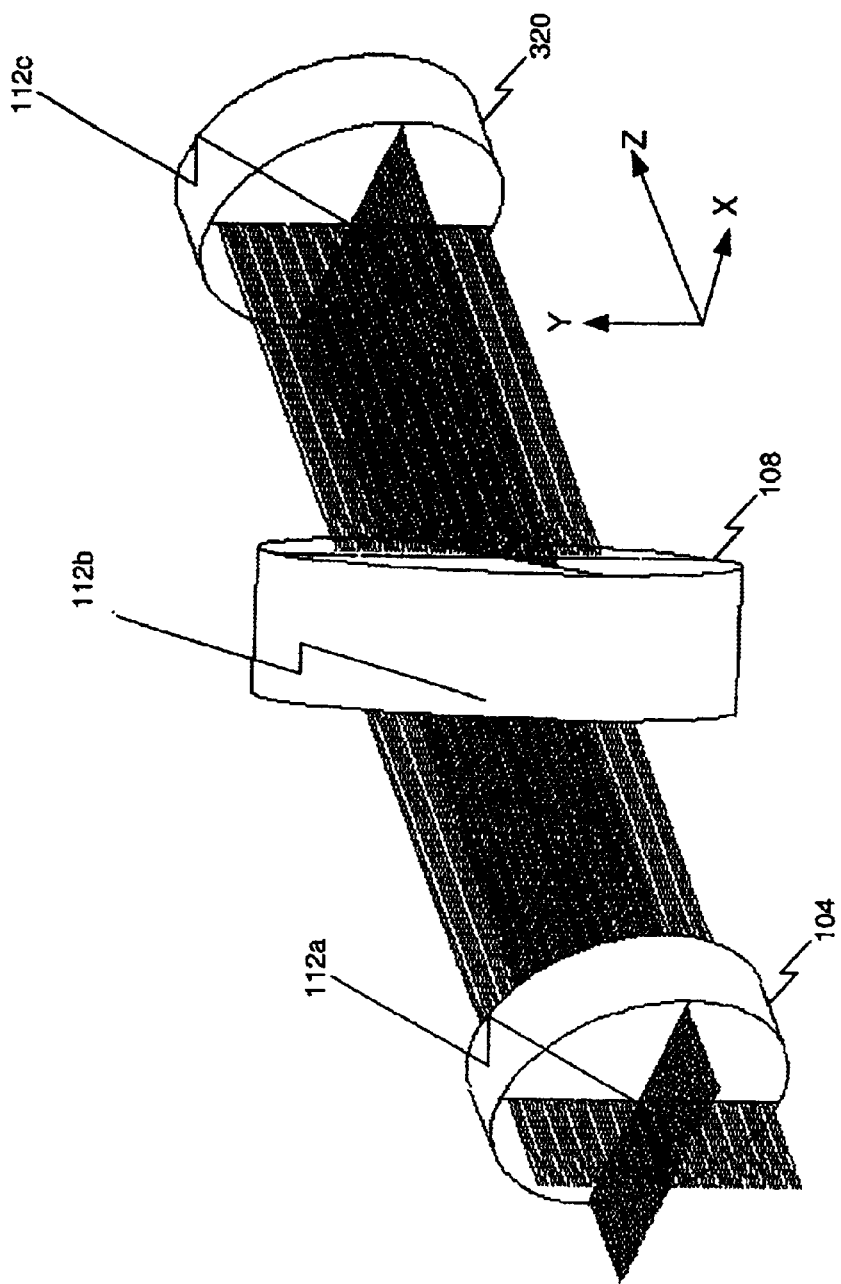
FIG. 10 shows an example of a three-dimensional implementation of an interferometric refractive index measurement system with an object comprising an optical material in a second tilted position upon the third axis, according to the present invention.

FIG. 10 illustrates a three-dimensional interferometric refractive index measurement system with the object 108 having a second tilted position about the third axis. In a preferred embodiment of the present invention the object 108 is tilted approximately 45 degrees about y axis towards the reference surface. A laser source (not shown in the figure) generates a reference wavefront that is reflected by the plurality of surfaces comprised by this interferometric arrangement. A phase difference measurement is performed for the wavefront reflected from the reference surface 104 and the wavefront reflected from the retro-mirror through the titled object 108. The collected interferometric data (denoted with $M_{10}$) is stored for later surface deformation determination. The position of the retro-mirror surface 320 is adjusted along x axis so that the fiducial marks 112a, 112b, 112c are aligned along one ray.

A three-dimensional analytical description of the inhomogeneity across the tested object can be made, according to a preferred embodiment of the present invention, using a set of polynomials orthogonal over the cylindrical volume of the tested object. According to one embodiment of the present invention, the 3D method determines the refractive index n of an object comprising an optical material using the following polynomial:

$$n(x, y, z) = n_0 + \sum_{i=1}^{s} P_i\left(\frac{x}{M_{xy}}, \frac{y}{M_{xy}}\right) \cdot \sum_{j=1}^{t} A_{ij} L_j\left(\frac{z}{M_z}\right), \quad \text{(EQ. 4)}$$

where x,y,z are coordinates of points determined in the Cartesian coordinate system; $P_i$ is the i-th Zernike polynomial orthogonal over the circle of unit radius (center of this circle coincides with the coordinate system origin); $L_j$ is the j-th Legendre polynomial orthogonal over the segment [0,1]; $M_{xy}$ is a normalization radius for Zernike polynomials; $M_z$ is a normalization coefficient for Legendre polynomials; $n_0$ is a bulk refractive index of a blank; $A_{ij}$ is a coefficient of approximation; s is a number of Zernike polynomials and t is a number of Legendre polynomials.

The coefficients $A_{ij}$ describe a radial refractive index distribution in the object, from i=1 to i=s when j=1. In this case, the refractive index does not depend on the z coordinate. If j>1, the above formula, equation 4, contains terms depending on all three coordinates.

The determination of the coefficients $A_{ij}$ is based on the plurality of measurements performed using a Fizeau interferometer for different angles of incidence and orientations of the object. The first four measurements, are described above, in conection with FIGS. 1–4 and establish the 2D refractive gradient index.

According to the present invention, additional measurements are performed for tilted positions of the object as illustrated above. In one embodiment, the determination of the 3D coefficients involves the determination surface deformation maps of the object and are computed using the following equations:

$$\Delta_0 = M_4 - \Delta_3, \quad \text{(EQ. 5)}$$

$$\Delta_1 = M_1 - M_4 + \Delta_3, \quad \text{(EQ. 6)}$$

$$\Delta_2 = M_3 - M_2 - \Delta_3, \quad \text{(EQ. 7)}$$

where $\Delta_0, \Delta_1, \Delta_2, \Delta_3$ are the surface deformations of to the reference surface, a first surface of the object, the second surface of the object and the retro-mirror, respectively. The surface map of deformation of the retro mirror, $\Delta_3$, is supposed to be known which means that the retro-mirror must be certified. [is certification of retro mirrors apparent to persons of ordinary skill in the art?]

In an embodiment of the present invention, the determination of the $A_{ij}$ coefficients is done using optical design program CODE V. The software used for calculation of $A_{ij}$ can be written in CODE V. The software allows modeling of the real measurements for the normal position and for the titled positions of the object. The measured interferograms and the calculated surface deformation maps (as illustrated above using equation 5 through 7) are used to define possible test schemes. With the help of an optimization procedure, such as the damped least square optimization procedure that is built in the CODE V optical design program, the $A_{ij}$ coefficients are defined. The optimization procedure is also used to minimize the difference between the measured and the modeled wavefronts for all object positions in order to calculate $A_{ij}$.

Figure 11:
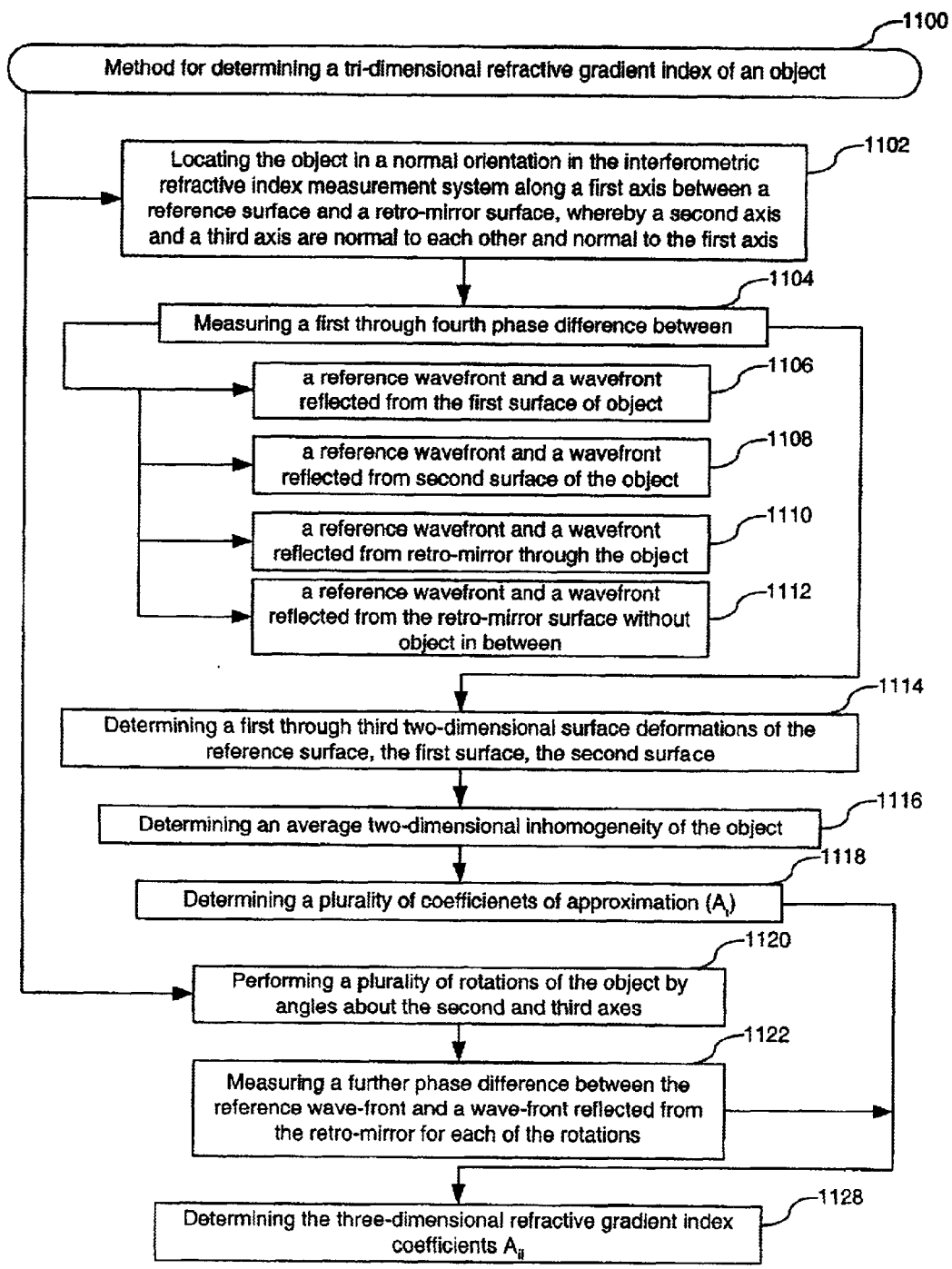
FIG. 11 illustrates a flow diagram for a method of determining a three-dimensional refractive gradient index on an object, according to the present invention.

FIG. 11 is a flow diagram for determining a three-dimensional refractive gradient index of an object. According to an exemplary embodiment of the present invention the method is implemented by a system that performs optical measurement relative to an object comprising an optical material which is coupled to a computer system for determining the properties of the object.

A method 1100 of FIG. 11 begins with step 1102. In step 1102, the object is located in a normal incidence in the interferometric refractive index measurement system along a first axis between a reference surface and a retro-mirror surface, whereby a second axis and a third axis are normal to each other and normal to the first axis.

In step 1104, a set of first through forth phase differences are measured. Step 1104 contains a plurality of sub-steps such as step 1106, 1108, 1110 and 1112. In step 1106, a phase difference is measured between a reference wavefront and from the reference surface and first surface of the object. In step 1108, a phase difference is measured between the reference wavefront and a wavefront reflected from a second surface of the object. In step 1110, a phase difference is measured between the reference wavefront and a wavefront reflected from retro-mirror through the object. In step 1112, a phase difference is measured between a reference wavefront and a wavefront reflected from a retro-mirror surface without object in between. In step 1114, based on the data previously determined in steps 1106, 1108, 1110 and 1112 the system determines a first through third two-dimensional surface deformations of reference surface $\Delta_0$ first object surface $\Delta_1$ and a second object surface $\Delta_2$. In step 1116, based on the determination made in step 1114, the system determines an average two-dimensional inhomogeneity of the object. In step 1118, based on the measurements made in steps 1104–1112 the system determines a plurality of coefficients of approximation. Method 1100 includes a second positioning step, step 1120, that involves performing a plurality of rotations of the object by angles about the second axis and the third axis.

In step 1122 further phase differences are measured between a reference wavefront and a wavefront reflected from the retro-mirror for each one of the plurality of rotations. In step 1128, a plurality of coefficients of approximation ($A_{ij}$) of the object is determined $A_{ij}$ determine tree-dimensional-dimensional refractive index distribution in the object.

Figure 12:
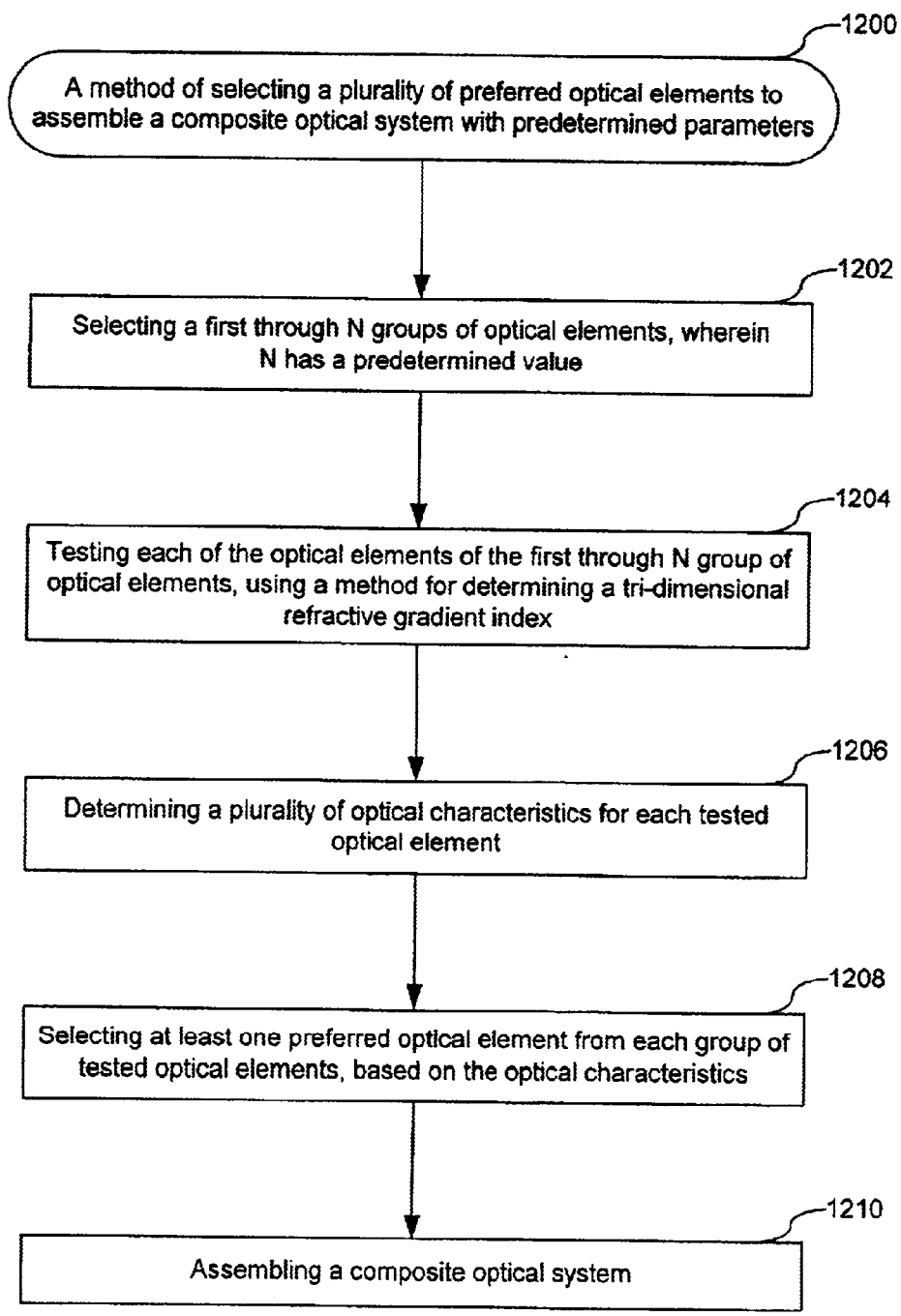
FIG. 12 illustrates a flow diagram for a method of selecting a plurality of preferred optical elements to assemble a composite optical system with predetermined parameters, according to the present invention.

FIG. 12 is directed to a further embodiment of the present invention. FIG. 12 depicts a flow diagram for selecting a plurality of preferred optical elements to assemble a composite optical system with predetermined parameters. A method 1200 comprises a plurality of steps.

In step 1202, a first through N groups of optical elements are selected, wherein N has a predetermined value. Each group corresponds to one optical element of an optical system. The optical system can be a lithography tool, for example, which comprises a plurality of optical elements. The method of FIG. 12 is used to characterize the 3D refractive gradient index of all the optical elements of each group. Thus, based on the collected data one optical element from each group can be selected based on its 3D refractive gradient index characteristics to meet predetermined design requirements to design/build an optical system.

Each of the optical elements of the first through the N-Th group of optical elements is tested using a method for determining a three-dimensional refractive gradient index of the optical element, as shown in step 1204.

In step 1206, a plurality of optical characteristics for each tested optical element is determined.

In step 1208, at least one preferred optical element from each of the first through N groups of tested optical elements is selected.

In step 1210, a composite optical system is assembled.

Example Computer System

Figure 13:
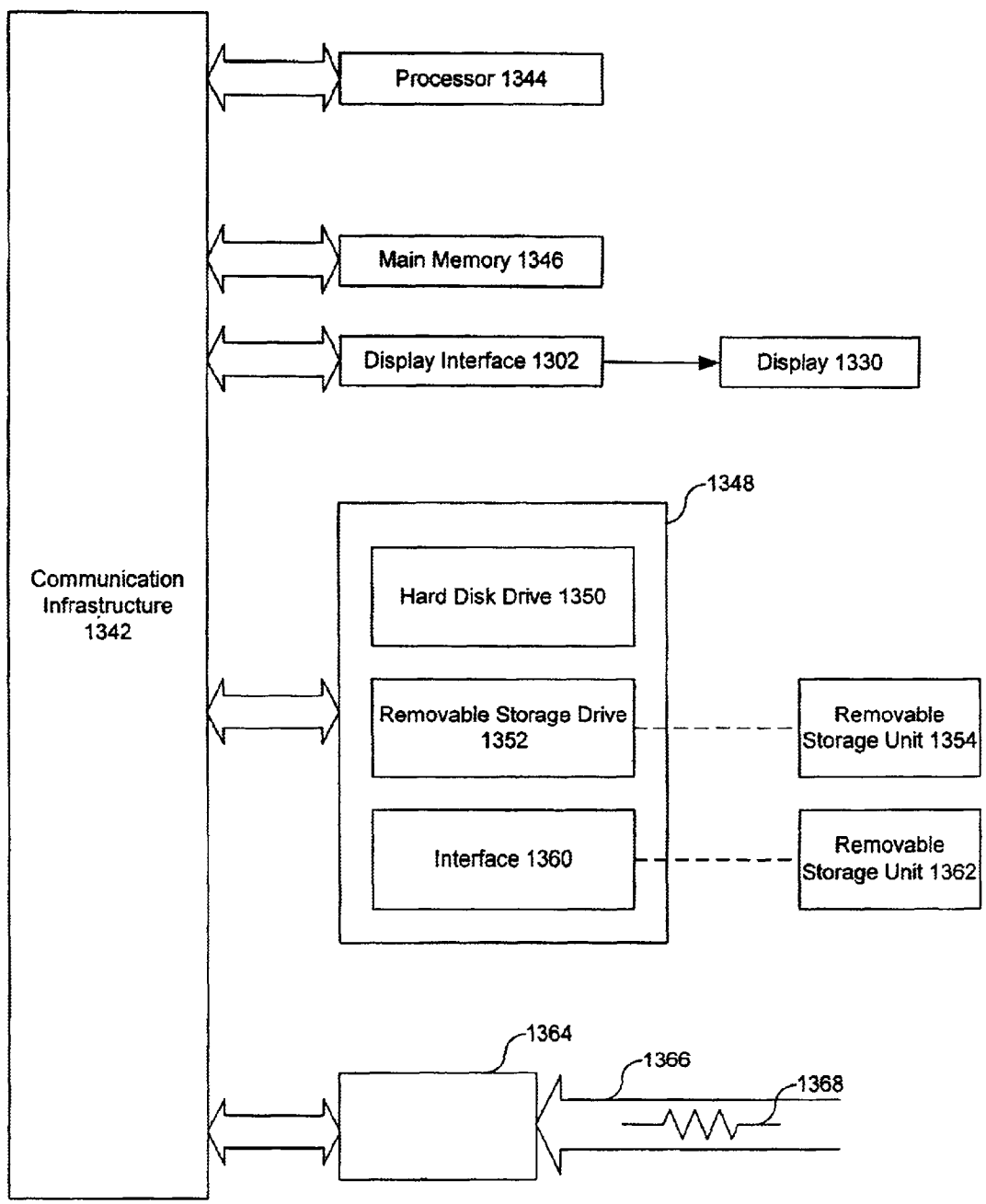
FIG. 13 illustrates an example computer system, according to an embodiment of the present invention.

The present invention (e.g. determining the $A_{ij}$ coefficients or like computational/determining steps) can be implemented using hardware, software or a combination thereof and may be implemented in one or more computer systems or other processing systems. An example of a computer system 1300 is shown in FIG. 13. The computer system 1300 represents any single or multi-processor computer. In conjunction, single-threaded and multi-threaded applications can be used. Unified or distributed memory systems can be used. Computer system 1300, or portions thereof, may be used to implement the present invention. For example, control and measurements performed in connection with the system of FIGS. 6–10 or the method of FIGS. 11–12 of the present invention can include software running on a computer system such as computer system 1300.

Computer system 1300 includes one or more processors, such as processor 1344. One or more processors 1344 can execute software implementing the routines described above. Each processor 1344 can be connected to a communication infrastructure 1342 (e.g., a communications bus, cross-bar, or network). Various software embodiments are described in terms of this exemplary computer system. After reading this description, it will become apparent to a person skilled in the relevant art how to implement the invention using other computer systems and/or computer architectures.

Computer system 1300 can include a display interface 1302 that forwards graphics, text, and other data from the communication infrastructure 1342 (or from a frame buffer not shown) for display on the display unit 1330.

Computer system 1300 also includes a main memory 1346, preferably random access memory (RAM), and can also include a secondary memory 1348. The secondary memory 1348 can include, for example, a hard disk drive 1350 and/or a removable storage drive 1352, representing a floppy disk drive, a magnetic tape drive, an optical disk drive, etc. The removable storage drive 1352 reads from and/or writes to a removable storage unit 1354 in a well-known manner. Removable storage unit 1354 represents a floppy disk, magnetic tape, optical disk, etc., which is read by and written to by removable storage drive 1352. As will be appreciated, the removable storage unit 1354 includes a computer usable storage medium having stored therein computer software and/or data.

In alternative embodiments, secondary memory 1348 may include other similar means for allowing computer programs or other instructions to be loaded into computer system 1300. Such means can include, for example, a removable storage unit 1362 and an interface 1360. Examples can include a program cartridge and cartridge interface (such as that found in video game console devices), a removable memory chip (such as an EPROM, or PROM) and associated socket, and other removable storage units 1362 and interfaces 1360 which allow software and data to be transferred from the removable storage unit 1362 to computer system 1300.

Computer system 1300 can also include a communications interface 1364. Communications interface 1364 allows software and data to be transferred between computer system 1300 and external devices via communications path 1366. Examples of communications interface 1364 can include a modem, a network interface (such as Ethernet card), a communications port, interfaces described above, etc. Software and data transferred via communications interface 1364 are in the form of signals which can be electronic, electromagnetic, optical or other signals capable of being received by communications interface 1364, via communications path 1366. Note that communications interface 1364 provides a means by which computer system 1300 can interface to a network such as the Internet.

In this document, the term "computer program product" is used to generally refer to removable storage unit 1354, a hard disk installed in hard disk drive 1350, or a carrier wave carrying software over a communication path 1366 (wireless link or cable) to communication interface 1364. A computer useable medium can include magnetic media, optical media, or other recordable media, or media that transmits a carrier wave or other signal. These computer program products are means for providing software to computer system 1300.

Computer programs (also called computer control logic) are stored in main memory 1346 and/or secondary memory 1348. Computer programs can also be received via communications interface 1364. Such computer programs, when executed, enable the computer system 1300 to perform the features of the present invention as discussed herein. In particular, the computer programs, when executed, enable the processor 1344 to perform features of the present invention. Accordingly, such computer programs represent controllers of the computer system 1300.

The present invention can be implemented as control logic in software, firmware, hardware or any combination thereof. In an embodiment where the invention is implemented using software, the software may be stored in a computer program product and loaded into computer system 1300 using removable storage drive 1352, hard disk drive 1350, or interface 1360. Alternatively, the computer program product may be downloaded to computer system 1300 over communications path 1366. The control logic (software), when executed by the one or more processors 1344, causes the processor(s) 1344 to perform functions of the invention as described herein.

In another embodiment, the invention is implemented primarily in firmware and/or hardware using, for example, hardware components such as application specific integrated circuits (ASICs). Implementation of a hardware state machine so as to perform the functions described herein will be apparent to persons skilled in the relevant art(s) from the teachings herein.

Conclusion

While specific embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A method for determining a three-dimensional refractive gradient index of an object, comprising an optical material, in an interferometric refractive index measurement system, comprising:

a. locating the object in a normal orientation in the interferometric refractive index measurement system along a first axis between a reference surface and a retro-mirror surface, whereby a second axis and a third axis are normal to each other and normal to said first axis;

b. measuring a first through forth phase differences, respectively, between a reference wavefront and a wavefront reflected from a first surface of the object, said reference wavefront and a wavefront reflected from a second surface of the object, said reference wavefront and a wavefront reflected from a retro-mirror through the object, and said reference wavefront and a wavefront reflected from said retro-mirror surface;

c. determining a first through third two-dimensional surface deformations of said reference surface, said first surface, and said second surface, and said retro-mirror surface, respectively, based on said first through forth phase differences;

d. determining an average two-dimensional inhomogeneity of the object based on said first through forth phase difference measurements;

e. determining a plurality of coefficients of approximation ($A_i$) of the object based on said average two-dimensional inhomogeneity;

f. performing a plurality of rotations of the object by angles about said second axis and said third axis;

g. measuring a further phase difference between said reference wavefront and a wavefront reflected from said retro-mirror for each one of said plurality of rotations;

h. determining a plurality of coefficients of approximation ($A_{ij}$) of the object based on said two-dimensional surface deformations and said phase difference measurements.

2. The methods of claim 1, further comprising providing lens blank object.

3. The methods of claim 1, further comprising providing a lens object.

4. The method of claim 1, further comprising providing the object as a cylindrical volume of optical material.

5. The method of claim 1, further comprising providing glass optical material.

6. The method of claim 1, further comprising providing plastic optical material.

7. The method of claim 1, further comprising providing the interferometric refractive index measurement system as one of a Fizeau interferometer, a Michaelson interferometer, a Twyman-Green interferometer, or a Mach-Zehnder interferometer.

8. The method of claim 1, wherein said first axis is the z of a Cartesian coordinate system.

9. The method of claim 1, wherein said second axis is the x of a Cartesian coordinate system.

10. The method of claim 1, wherein said third axis is the y of a Cartesian coordinate system.

11. The method of claim 1, further comprising the step of generating said reference wave-front with a laser source.

12. The method of claim 1, further comprising performing step d using Zernike polynomials.

13. The of claim 1, further comprising performing step e using Least Square method.

14. The method of claim 1, wherein step f comprises rotating the object by a first angle about the second axis.

15. The method of claim 14, further comprising rotating said first angle to about 45 degrees towards said retro-mirror.

16. The method of claim 1, wherein step f comprises rotating the object by a second angle about said second axis.

17. The method of claim 16, further comprising rotating said second angle to about 45 degrees towards said reference surface.

18. The method of claim 1, wherein step f comprises rotating the object by a first angle about said third axis.

19. The method of claim 18, further comprising rotating said first angle to about 45 degrees towards said retro-mirror.

20. The method of claim 1, wherein step f comprises rotating the object by a second angle about said third axis.

21. The method of claim 20, further comprising rotating said second angle to about 45 degrees towards said reference surface.

22. The method of claim 1, wherein step f further comprises aligning said retro-mirror with the direction of light.

23. The method of claim 1, wherein step i is performed using an iterative procedure.

24. The method of claim 23, wherein step i further comprises performing a CODE V damped least square algorithm.

25. A method of selecting a plurality of preferred optical elements to assemble a composite optical system with predetermined parameters, comprising the steps of:

a. selecting a first through N groups of optical elements, wherein N has a predetermined value;

b. testing each of the optical elements of said first through N group of optical elements, using a method according to claim 1;

c. determining a plurality of optical characteristics for each tested optical element;

d. selecting at least one preferred optical element from each of said first through N groups of tested optical elements, based on said optical characteristics; and e. assembling a composite optical system.

* * * * *

UNITED STATES PATENT AND TRADEMARK OFFICE
CERTIFICATE OF CORRECTION

PATENT NO. : 6,741,362 B2
DATED : May 25, 2004
INVENTOR(S) : Smirnov et al.

It is certified that error appears in the above-identified patent and that said Letters Patent is hereby corrected as shown below:

Title page, Item [54] and Column 1, lines 1-3,
Title, "METHOD, SYSTEM, AND COMPUTER PROGRAM PRODUCT FOR DETERMINING REFRACTIVE INDEX DISTRIBUTION" should be replaced with -- METHOD FOR DETERMINING REFRACTIVE INDEX DISTRIBUTION --.

Column 1,
Line 17, "microlitography" should be replaced with -- microlithography --.
Lline 60, "forth" should be replaced with -- fourth --.

Column 2,
Line 1, "forth" should be replaced with -- fourth --.

Column 3,
Line 61, "Gradient index (GRIN) measurements" is a subtitle.

Column 4,
Line 48, "i" is subscript in "Ai".

Column 5,
Line 58, "almost" should be replaced with -- ideal --.

Column 6,
Line 17, "almost" should be replaced with -- ideal --.

Column 8,
Line 7, exclude struck out z symbol.

Column 9,
Line 8, insert -- of -- after "determination".
Line 22, delete "[is certification of retro mirrors apparent to".
Line 23, delete "persons of ordinary skill in the art?]".
Line 52, "forth" should be replaced with -- fourth --.
Line 67, insert "," before "$\Delta$".

UNITED STATES PATENT AND TRADEMARK OFFICE
CERTIFICATE OF CORRECTION

PATENT NO. : 6,741,362 B2
DATED : May 25, 2004
INVENTOR(S) : Smirnov et al.

It is certified that error appears in the above-identified patent and that said Letters Patent is hereby corrected as shown below:

Column 10,
Line 13, place "." after "of the object is determined."
Line 14, "determined $A_{ij}$ determine" should be replaced with -- determined to estimate a three dimensional --.
Line 15, delete "tree-dimensional-dimensional".
Line 32, "N-Th" should be replaced with -- N-th --.

Column 12,
Line 38, "forth" should be replaced with -- fourth --.
Line 38, "differences" should be replaced with -- difference --.
Line 39, delete "respectively,".
Line 50, delete "respectively,".
Line 50, "forth" should be replaced with -- fourth --.
Line 52, "forth" should be replaced with -- fourth --.

Column 13,
Line 1, delete "further comprising providing".
Line 2, -- wherein said object is a -- should be inserted before "lens".
Line 3, delete "further comprising providing".
Line 4, -- wherein said object is -- should be inserted before "a".
Line 5, delete "further comprising providing the".
Line 6, insert -- wherein said -- before "object".
Line 6, "as" should be replaced with -- is --.
Line 7, delete "further comprising providing".
Line 8, insert -- wherein said object is a -- before "glass".
Line 9, delete "further comprising providing".
Line 10, insert -- wherein said object is a -- before "plastic".
Line 11, delete "further comprising providing the".
Line 12, insert -- wherein said -- before "interferometric".
Line 25, "step d using Zernike polynimials" should be replaced with -- step e using Zernike polynimials --.
Line 26, insert -- method -- after "13. The".

UNITED STATES PATENT AND TRADEMARK OFFICE
CERTIFICATE OF CORRECTION

PATENT NO. : 6,741,362 B2
DATED : May 25, 2004
INVENTOR(S) : Smirnov et al.

It is certified that error appears in the above-identified patent and that said Letters Patent is hereby corrected as shown below:

Column 14,
Line 13, "23. The method of claim 1, wherein step i" should be replaced with -- 23. The method of claim 1, wherein step h --.
Line 15, "24. The method of claim 23, wherein step i" should be replaced with -- 24. The method of claim 23, wherein step h --.

Signed and Sealed this

Fifteenth Day of March, 2005

JON W. DUDAS
*Director of the United States Patent and Trademark Office*